United States Patent
Thornton et al.

(10) Patent No.: US 7,318,945 B2
(45) Date of Patent: Jan. 15, 2008

(54) LAMINATED DRUG-POLYMER COATED STENT HAVING DIPPED LAYERS

(75) Inventors: Ronan M. Thornton, Galway (IE); Finbar Dolan, County Westmeath (IE)

(73) Assignee: Medtronic Vascular, Inc., Santa Rosa, CA (US)

(*) Notice: Subject to any disclaimer, the term of this patent is extended or adjusted under 35 U.S.C. 154(b) by 856 days.

(21) Appl. No.: 10/674,293

(22) Filed: Sep. 29, 2003

(65) Prior Publication Data

US 2005/0010282 A1 Jan. 13, 2005

Related U.S. Application Data

(60) Provisional application No. 60/485,766, filed on Jul. 9, 2003.

(51) Int. Cl.
*A61L 33/00* (2006.01)
(52) U.S. Cl. ............................ 427/2.24; 623/1.46
(58) Field of Classification Search .............. 623/1.44, 623/1.46; 427/2.24, 2.25, 2.3, 2.28, 421, 427/235; 424/422, 423
See application file for complete search history.

(56) References Cited

U.S. PATENT DOCUMENTS

| | | | |
|---|---|---|---|
| 5,980,972 A | 11/1999 | Ding | |
| 6,153,252 A | 11/2000 | Hossainy et al. | |
| 6,214,115 B1 | 4/2001 | Taylor et al. | |
| 6,251,136 B1 | 6/2001 | Guruwaiya | |
| 6,258,121 B1 * | 7/2001 | Yang et al. | 623/1.46 |
| 6,306,166 B1 | 10/2001 | Barry et al. | |
| 6,344,035 B1 | 2/2002 | Chudzik et al. | |
| 6,358,556 B1 | 3/2002 | Ding et al. | |
| 6,517,889 B1 | 2/2003 | Javaraman | |
| 6,656,517 B2 * | 12/2003 | Michal et al. | 427/2.24 |
| 2002/0082679 A1 | 6/2002 | Sirhan et al. | |

FOREIGN PATENT DOCUMENTS

| | | |
|---|---|---|
| EP | 0701802 | 3/1996 |
| WO | WO 02/074194 | 9/2002 |
| WO | WO 03/047636 | 6/2003 |

* cited by examiner

*Primary Examiner*—Kevin T. Truong

(57) ABSTRACT

The present invention provides a method of applying a drug-polymer coating on a stent. A stent framework is dipped into a first polymeric solution including a first polymer, a first therapeutic agent, and a first solvent. The polymeric solution is dried to form a thin drug-polymer layer on the stent framework. The stent framework with the thin drug-polymer layer, which is insoluble in the second polymeric solution, is dipped into a second polymeric solution including a second polymer and a second solvent and is dried to form a thin barrier layer on the thin drug-polymer layer. The steps of dipping the stent framework into the first polymeric solution, drying the first polymeric solution, dipping the stent framework into the second polymeric solution, and drying the second polymeric solution are repeated until a target drug-polymer coating thickness is disposed on the stent framework.

11 Claims, 7 Drawing Sheets

- 710: Select Polymers, Therapeutic Agents, Solvents and Concentrations
- 720: Fabricate Drug-Polymer Coated Stent
- 730: Insert Drug-Polymer Coated Stent into Body
- 740: Elute Therapeutic Agent(s)

LAMINATED DRUG-POLYMER COATED STENT HAVING DIPPED LAYERS

CROSS-REFERENCE TO RELATED APPLICATION

This application claims the benefit of U.S. provisional patent application Ser. No. 60/485,766, filed Jul. 9, 2003, the contents of which are hereby incorporated by reference.

FIELD OF THE INVENTION

This invention relates generally to biomedical stents. More specifically, the invention relates to a laminated drug-polymer coating disposed on an endovascular stent for in vivo, time-release drug delivery, and methods of coating thereof.

BACKGROUND OF THE INVENTION

Endovascular stents have become increasingly important in medical procedures to restore the function of bodily lumens. With generally open tubular structures, the stents typically have apertured or lattice-like walls of a metallic or polymeric base, and can be either balloon expandable or self-expanding. A stent is typically deployed by mounting the stent on a balloon portion of a balloon catheter, positioning the stent in a body lumen, and expanding the stent by inflating the balloon. The balloon is then deflated and removed, leaving the stent in place. Stents help reduce the probability and degree of vessel blockage from restenosis.

An increasing number of stents for treating vascular conditions are being coated with protective materials and bioactive drugs. A variety of stent coatings and compositions have been proposed to provide localized therapeutic pharmacological agents and treatment of a vessel at the site being supported by the stent. Stent coatings with various families of drug polymer chemistries have been used to increase the effectiveness of stenting procedures and to control drug-elution properties. For example, polymeric coatings can be made from polyurethane, polyester, polylactic acid, polyamino acid, polyorthoester, and polyphosphate ester. Examples of drug or bioactive agents include antirestenotic and anti-inflammatory compounds.

Medical research indicates a greater effectiveness of vascular stents when stents are coated with pharmaceutical drugs that help prevent or treat medical conditions such as restenosis and thrombosis. These drugs may be released from a coating while in the body, delivering their patent effects at the site where they are most needed. The localized levels of the medications can be elevated, and are therefore potentially more effective than orally or intravenously delivered drugs. Furthermore, drugs released from tailored stent coatings can have controlled, timed-release qualities, eluting their bioactive agents over hours, weeks or even months. Stent coatings typically have a drug or active agent, which has been dissolved or dispersed throughout the polymeric material and physically constrained within the polymer. The sustained release of drugs generally relies upon either degradation of the polymer or diffusion through the polymer to control the elution of the compounds.

Drug polymer coatings on medical devices such as stents and catheters need to be mechanically pliant because the devices undergo significant flexion or expansion during the delivery and deployment. A stent deployed by self-expansion or balloon expansion is accompanied by a high level of bending at portions of the stent framework, which can cause cracking, flaking, peeling, or delaminating of many candidate drug polymers when the stent diameter is increased by threefold or more during expansion. In addition, any step within the process for coating a pre-deployed stent should not cause a drug-polymer to fall off, crystallize or melt. Chudzik et al. disclose a flexible coating composition to address the need for pliancy in "Bioactive Agent Release Coating", U.S. Pat. No. 6,344,035 issued Feb. 5, 2002. The bioactive agent or drug is in combination with a mixture of polymers such as poly(butyl methacrylate) and poly(ethylene-co-vinyl acetate). Polymers for use as stent coatings need to demonstrate characteristics of biocompatibility, good drug release as well as flexibility.

In selecting polymers for drug delivery and applying drug coatings to stents, certain criteria must be met: polymer biocompatibility, satisfactory mechanical properties such as durability and integrity during roll down and expansion of the stent, and correct release profiles for the drugs. Candidate chemistries for drug polymers may result in excessively rapid elution of an incorporated drug. When a drug is eluted too quickly, it may be ineffective and may fail to achieve the desired effect in the surrounding tissue bed. If a drug is eluted too slowly, the pharmaceutical intent may remain unfulfilled. Furthermore, incorporation of more than one drug in the same coating can result in a much faster elution rate than a second drug in the same drug polymer, making the controlled delivery of multiple drugs difficult. Even pharmaceutical compounds with nearly the same pharmaceutical effect can have dramatically different elution rates in the same coating chemistry, depending on the formation of the compounds.

Stents can be coated with a polymer or combination of a polymer and a pharmaceutical agent or drug by application techniques such as dipping, spraying, painting, and brushing. In many of the current medical device or stent coating methods, a composition of a drug and a polymer in a solvent is applied to a device to form a substantially uniform layer of drug and polymer. A common solvent for the polymers and drugs employed is usually required, and techniques have been developed to micronize the drugs into small particles so that the drugs can be suspended in the polymer solution. Micronization can be time consuming, and may result in a degradation or loss of desired therapeutic properties of the drug. A method of using micronized drugs and layering a drug-coated stent using pharmacological and polymeric agents is described by Guruwaiya et al. in U.S. Pat. No. 6,251,136 issued Jun. 26, 2001. A pharmacological agent is applied to a stent in dry, micronized form over a sticky base coating. A membrane-forming polymer, selected for its ability to allow the diffusion of the pharmacological agent therethrough, is applied over the entire stent. More specifically, a stent, typically a metal stent, has a layer of a sticky material applied to selected surfaces of the stent. A pharmacological agent is layered on the sticky material and a membrane forming a polymer coating is applied over the pharmacological agent. The membrane is formed from a polymer that permits diffusion of the pharmacological agent over a predetermined time period.

A method of applying drug-release polymer coatings that uses solvents is described in "Method of Applying Drug-Release Coatings", Ding et al., U.S. Pat. No. 5,980,972 issued Nov. 9, 1999. A polymer is dissolved in one solvent and a drug is dissolved or suspended in a similar or different type of solvent. The solutions are applied either sequentially or simultaneously onto the devices by spraying or dipping to form a substantially homogenous composite layer of the polymer and the biologically active material.

Many of the drug-coated stents in recent years have been sprayed with rather than dipped in a drug-polymer solution. Spray coating, a currently preferred method for coating stents, can result in a significant amount of spray material lost during the process and when expensive drugs are used in these coatings, the use of spray coating may be costly.

Dip coating was used with early stents and other medical-device designs that were of relatively open construction fabricated from wires or from ribbons. Dipped coatings with relatively low coating weights, for example, coatings with about 4% polymer, were used with some occurrences of bridging or webbing of the coating in the open spaces or slots between the structural members of the device. Such coating methods were performed by manually dipping the stent in a liquid, and then removing the stent and drying it. The dipping process requires care to avoid excess liquid on the stent framework or inconsistent drying of the liquid, otherwise the apertures can become blocked unnecessarily. Applying a thick coating tends to exacerbate webbing and bridging problems, and increasing the solids content of the coating solution also increases webbing and bridging between the struts. Any coating method needs to avoid webbing, as well as control the weight and thickness of a coating.

Problems of webbing and having excess coating material on stent struts are recognized by those skilled in the art of manufacturing stents. For example, a manual-dipping process step that blows excess material off the open framework of a tubular stent is disclosed in "Coating" by Taylor et al., U.S. Pat. No. 6,214,115 issued Apr. 10, 2001. The process addresses the problems of inconsistent drying and blockage of openings. Another dipping process that addresses the issues of blockage and bridging between the stent struts is disclosed by Hossainy et al. in "Process for Coating Stents", U.S. Pat. No. 6,153,252 issued Nov. 28, 2000. Flow or movement of the coating fluid through the openings in the perforated medical device is used to avoid the formation of blockages or bridges. The flow system may use a perforated manifold inserted in the stent to circulate the coating fluid, or may place the stent on a mandrel or in a small tube that is moved relative to the stent during the coating process.

Newer stents that are of less open construction, such as catheter-deployed, self-expanding stents are more difficult to coat evenly using a dipping method. Nevertheless, one advantage of dip coating is the ability to process a greater number of stents in a more efficient manufacturing process.

A stent with a single coating having at least one therapeutic agent is described by Sirhan and Yan in "Delivery or Therapeutic Capable Agents", U.S. Patent Application No. 20020082679 published Jun. 27, 2002. Barry and others describe another polymer composition that can be used for delivering substantially water-insoluble drugs in "Loading and Release of Water-Insoluble Drugs", U.S. Pat. No. 6,306, 166 issued Oct. 23, 2001. A medical device is coated with one or more layers of a volatile organic solution comprising a polyvinyl aromatic polymer and an antineoplastic chemotherapy drug such as paclitaxel. In the descriptions of the aforementioned coatings, dipping is given as one of the methods for applying the drug-polymer coating to the device, although the disclosures do not address the potential problem of webbing or bridging in the open areas of stent structures, particularly when multiple coats are applied.

Jayaraman proposes a solution to the webbing or bridging issue in "Process for Coating a Surface of a Stent", U.S. Pat. No. 6,517,889 issued Feb. 11, 2003. The coating process includes inserting a thread through the lumen of the stent and producing relative motion between the stent and the thread to remove coating material located within the openings of the stent.

Multiple dips can be used to build up the weight and thickness of the coating, but each subsequent dip may affect the coating already deposited. A coating can re-dissolve in a second coating solution, causing some loss of the first layer of coating. Also, applications of multiple dip coats from low concentration solutions can have the effect of reaching a limiting loading level as equilibrium is reached between the solution concentration and the amount of coating with or without a pharmaceutical agent. One such method that applies a plurality of relatively thin coatings on an open-lattice stent is disclosed in "Drug Release Stent Coating", Ding et al., U.S. Pat. No. 6,358,556 issued Mar. 19, 2002. The stents are coated by dipping or preferably spraying the stent with a solvent mixture of uncured polymeric silicone material with a crosslinker and a finely divided biologically active species. The method includes a step for sterilizing with an inert argon gas plasma and exposure to gamma radiation. Potential problems with bridging or webbing in the lattice framework are not addressed.

Accordingly, what is needed is a more efficient manufacturing method for coating medical devices such as stents that can apply drug-polymer coatings without creating undesirable bridging or webbing. An improved process provides coatings that are well adhered and flexible, a well as controls coating properties such as thickness, porosity, and smoothness. An improved stent with one or more drug-polymer coatings maintains mechanical integrity during its deployment, provides a desired elution rate for one or more drugs, and overcomes the deficiencies and limitations described above.

SUMMARY OF THE INVENTION

One aspect of the invention provides a method of applying a drug-polymer coating on a stent. A stent framework is dipped into a first polymeric solution comprising a first polymer, a first therapeutic agent, and a first solvent. The first polymeric solution is dried to form a thin drug-polymer layer on the stent framework. The stent framework including the thin drug-polymer layer is dipped into a second polymeric solution comprising a second polymer and a second solvent. The second polymeric solution is dried to form a thin barrier layer on the thin drug-polymer layer. The thin drug-polymer layer is insoluble in the second polymeric solution. The dipping and drying steps are repeated until a target drug-polymer coating thickness is disposed on the stent framework.

Another aspect of the invention provides a drug-polymer coated stent including a stent framework and a laminated drug-polymer coating disposed on the stent framework. The laminated drug-polymer coating includes a plurality of thin drug-polymer layers positioned between thin barrier layers. The thin drug-polymer layers include a first therapeutic agent and a first polymer. The thin barrier layers include a second polymer.

Another aspect of the invention is a system for treating a vascular condition, including a catheter and a coated stent coupled to the catheter. The coated stent includes a stent framework and a laminated drug-polymer coating disposed on the stent framework. The laminated drug-polymer coating has a plurality of thin drug-polymer layers including a first therapeutic agent and a first polymer positioned between thin barrier layers that include a second polymer.

Another aspect of the invention is a method of treating a vascular condition. A drug-polymer coated stent, which is inserted within a vessel of a body, includes a laminated drug-polymer coating having thin drug-polymer layers with a therapeutic agent and a first polymer, and thin barrier layers with a second polymer. At least one therapeutic agent is eluted from the laminated drug-polymer coating into the body.

The present invention is illustrated by the accompanying drawings of various embodiments and the detailed description given below. The drawings should not be taken to limit the invention to the specific embodiments, but are for explanation and understanding. The detailed description and drawings are merely illustrative of the invention rather than limiting, the scope of the invention being defined by the appended claims and equivalents thereof. The foregoing aspects and other attendant advantages of the present invention will become more readily appreciated by the detailed description taken in conjunction with the accompanying drawings.

BRIEF DESCRIPTION OF THE DRAWINGS

Various embodiments of the present invention are illustrated by the accompanying figures, wherein:

FIG. 7 is a flow diagram of a method for treating a vascular condition, in accordance with one embodiment of the current invention.

DETAILED DESCRIPTION OF THE PRESENTLY PREFERRED EMBODIMENTS

Figure 1:
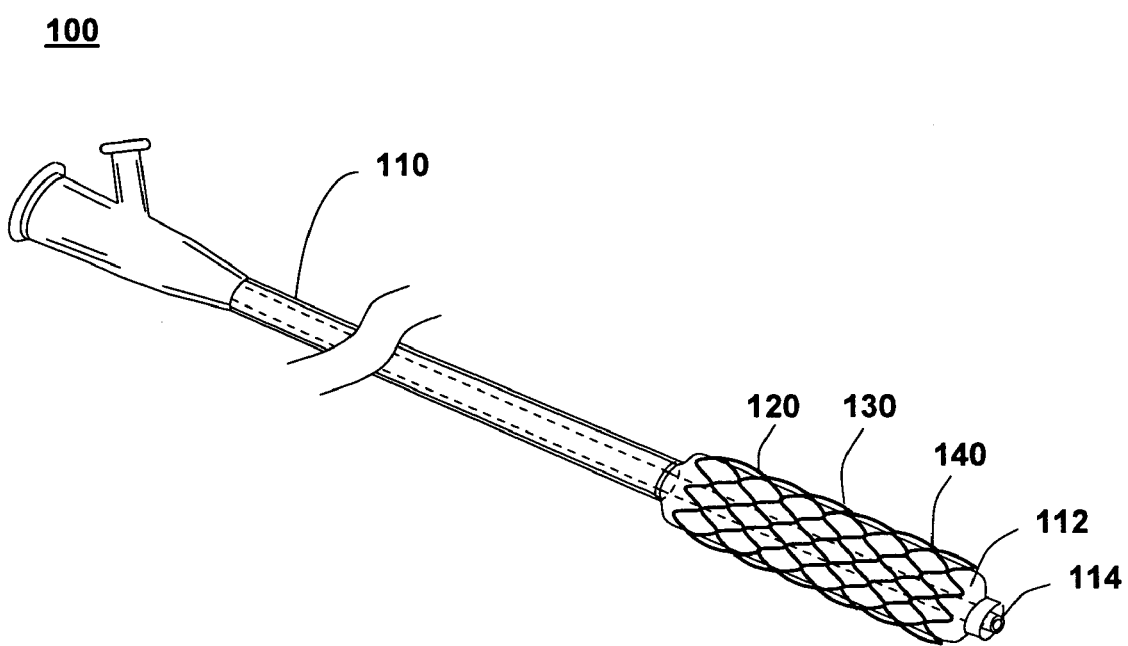
FIG. 1 is an illustration of a system for treating a vascular condition including a drug-polymer coated stent coupled to a catheter, in accordance with one embodiment of the current invention.

FIG. 1 shows an illustration of a system for treating a vascular condition, comprising a drug-polymer coated stent coupled to a catheter, in accordance with one embodiment of the present invention at 100. Coated stent with catheter 100 includes a drug-polymer coated stent 120 coupled to a delivery catheter 110. Drug-polymer coated stent 120 includes a stent framework 130 and a laminated drug-polymer coating 140 disposed on the stent framework. Laminated drug-polymer coating 140 includes a plurality of thin drug-polymer layers positioned between thin barrier layers. The drug-polymer layers include a therapeutic agent and a first polymer. The barrier layers include a second polymer that may also include a second therapeutic agent. The constituents of drug-polymer coated stent 120 are selected to minimize leaching of drug or polymer from underlying layers when forming the multi-layer dip-coated stent.

Insertion of coated stent 120 into a vessel in the body helps treat, for example, heart disease, various cardiovascular ailments, and other vascular conditions. Catheter-deployed coated stent 120 typically is used to treat one or more blockages, occlusions, stenoses, or diseased regions in the coronary artery, femoral artery, peripheral arteries, and other arteries in the body. Treatment of vascular conditions may include the prevention or correction of various ailments and deficiencies associated with the cardiovascular system, the cerebrovascular system, urinogenital systems, biliary conduits, abdominal passageways and other biological vessels within the body.

An exemplary laminated drug-polymer coating 140 includes or encapsulates one or more therapeutic agents. Laminated drug-polymer coating 140 may comprise one or more therapeutic agents dispersed within or encased by drug-polymer layers or barrier layers on coated stent 120, which are eluted from coated stent 120 with controlled time delivery after deployment of coated stent 120 into the body. A therapeutic agent is capable of producing a beneficial effect against one or more conditions including coronary restenosis, cardiovascular restenosis, angiographic restenosis, arteriosclerosis, hyperplasia, and other diseases or conditions. For example, the therapeutic agent can be selected to inhibit or prevent vascular restenosis, a condition corresponding to a narrowing or constriction of the diameter of the bodily lumen where the stent is placed. Laminated drug-polymer coating 140 may comprise, for example, an antirestenotic agent such as rapamycin, a rapamycin derivative, or a rapamycin analog to prevent or reduce the recurrence of narrowing and blockage of the bodily vessel. Laminated drug-polymer coating 140 may comprise an anti-cancer drug such as camptothecin or other topoisomerase inhibitors, an antisense agent, an antineoplastic agent, an antiproliferative agent, an antithrombogenic agent, an anticoagulant, an antiplatelet agent, an antibiotic, an anti-inflammatory agent, a steroid, a gene therapy agent, an organic drug, a pharmaceutical compound, a recombinant DNA product, a recombinant RNA product, a collagen, a collagenic derivative, a protein, a protein analog, a saccharide, a saccharide derivative, a bioactive agent, a pharmaceutical drug, a therapeutic substance, or a combination thereof.

The elution rates of the therapeutic agents and total drug eluted into the body and the tissue bed surrounding the stent framework are based on the target thickness of laminated drug-polymer coating 140, the constituency and individual layer thicknesses of laminated drug-polymer coating 140, the nature and concentration of the therapeutic agents, the thickness and composition of any cap coat, and other factors. Laminated drug-polymer coating 140 may include and elute multiple therapeutic agents to achieve the desired therapeutic effect. Laminated drug-polymer coating 140 can be tailored to control the elution of one or more therapeutic agents primarily by diffusion processes. In some cases, a portion of the polymeric coating is absorbed into the body, releasing therapeutic agents from within the coating. The barrier layers can be selected to provide a diffusion barrier to the therapeutic agents and slow drug elution.

Incorporation of a drug or other therapeutic agent into laminated drug-polymer coating 140 allows, for example, the rapid delivery of a pharmacologically active drug or bioactive agent within twenty-four hours following the deployment of a stent, with a slower, steady delivery of a second bioactive agent over the next three to six months. In one example, a first therapeutic agent comprises an antirestenotic drug such as rapamycin, a rapamycin derivative, or a rapamycin analog. The second therapeutic agent may comprise, for example, an anti-cancer drug such as camptothecin or other topoisomerase inhibitors. The therapeutic agent constituency in the drug-polymer layers may be, for example, between 0.1 percent and 50 percent of the drug-polymer layer by weight. In another example, the first therapeutic agent comprises an anti-proliferative compound such as 5-fluorouracil, with an optional second therapeutic agent such as rapamycin, a rapamycin derivative, a rapamycin analog, or dexamethosone. In another example, the first therapeutic agent comprises an anti-inflammatant such as dexamethasone, and an optional second therapeutic agent such as 5-fluorouracil.

Catheter 110 of an exemplary embodiment of the present invention includes a balloon 112 that expands and deploys the stent within a vessel of the body. After positioning coated stent 120 within the vessel with the assistance of a guide wire traversing through a guidewire lumen 114 inside catheter 110, balloon 112 is inflated by pressurizing a fluid such as a contrast fluid that fills a tube inside catheter 110 and balloon 112. Coated stent 120 is expanded until a desired diameter is reached, and then the contrast fluid is depressurized or pumped out, separating balloon 112 from coated stent 120 and leaving coated stent 120 deployed in the vessel of the body. Alternately, catheter 110 may include a sheath that retracts to allow expansion of a self-expanding version of coated stent 120.

Figure 2:
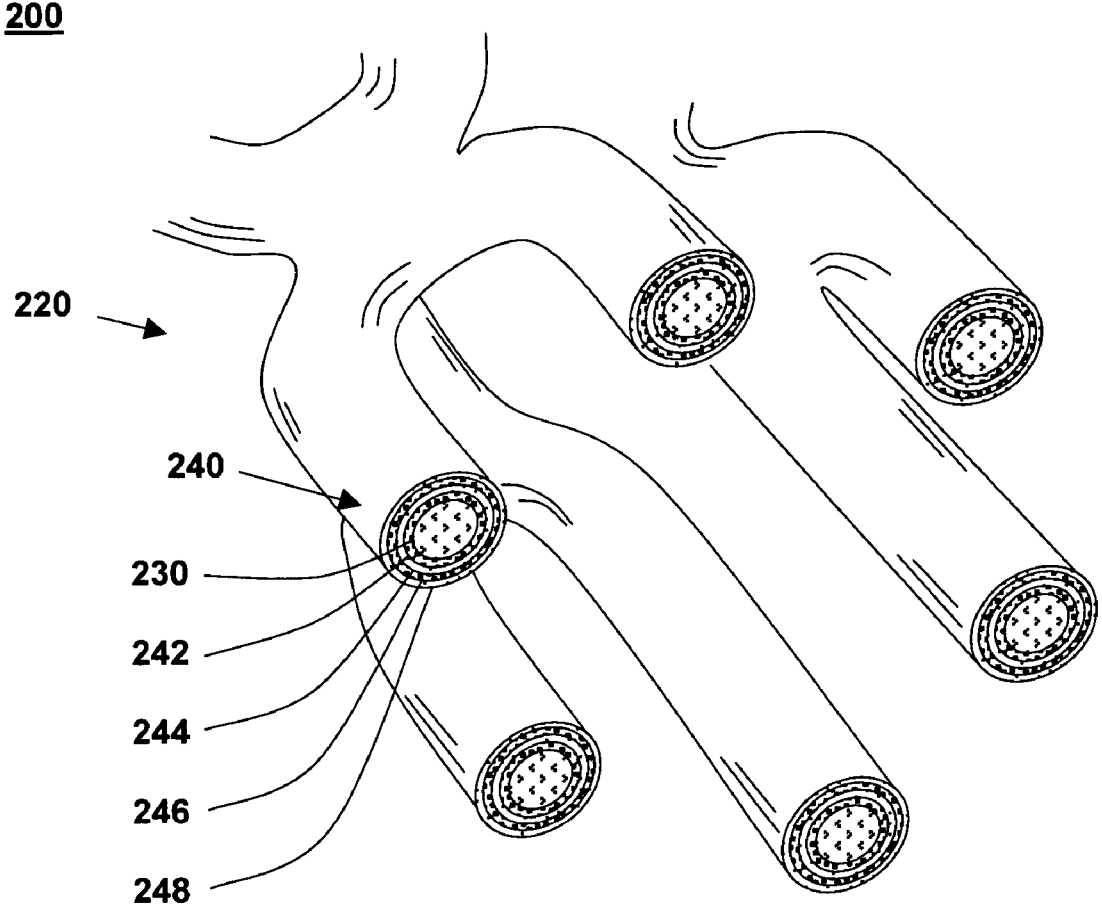
FIG. 2 is a cross-sectional perspective view of a drug-polymer coated stent, in accordance with one embodiment of the current invention.

FIG. 2 shows a cross-sectional perspective view of a drug-polymer coated stent, in accordance with one embodiment of the present invention at 200. A drug-polymer coated stent 220 includes a stent framework 230 with a laminated drug-polymer coating 240 disposed on stent framework 230. Laminated drug-polymer coating 240 includes a plurality of thin drug-polymer layers 242 and 246 that are positioned between thin barrier layers 244 and 248. Drug-polymer layers 242 and 246 include a combination or mixture of a first therapeutic agent and a first polymer, and barrier layers 244 and 248 include a second polymer.

Although illustrated with two sets of drug-polymer layers and barrier layers, multiple sets of coating layers may be disposed on stent framework 230. For example, ten sets of layers, each layer on the order of 0.1 micrometers thick, can be alternately disposed on stent framework 230 to produce a two-micrometer thick coating. In another example, twenty sets of layers, each layer on the order of 0.5 micrometers thick, can be alternately disposed on stent framework 230 to produce a twenty-micrometer thick coating. The drug-polymer layers and the barrier layers need not be the same thickness, and the thickness of each may be varied throughout laminated drug-polymer coating 240. Alternately, the first coating layer may be a barrier layer, and the final coating layer may comprise, for example, a thick cap coat.

Stent framework 230 comprises a metallic base or a polymeric base, such as stainless steel, nitinol, tantalum, MP35N alloy, platinum, titanium, a chromium-based alloy, a suitable biocompatible alloy, a suitable biocompatible material, a biocompatible polymer, or a combination thereof. The polymeric base material may comprise any suitable polymer for biomedical stent applications, as is known in the art.

In one example, drug-polymer layers 242 and 246 comprise a first polymer such as poly(ethylene-vinyl acetate) (PEVA) and a first therapeutic agent such as camptothecin, rapamycin, a rapamycin derivative, or a rapamycin analog. Barrier layers 244 and 248 comprise a second polymer such as polyurethane, polycaprolactone, or a blended polymer of polyurethane and polycaprolactone that can be selected based on a predetermined elution rate. For example, tailoring the fraction of the two polymers, the thickness of the drug-polymer layers and the barrier layers, or the concentration of the therapeutic agents controls the elution rate of one or more therapeutic agents dispersed within or encased by laminated drug-polymer coating 240. Drug elution refers to the transfer of a therapeutic agent from laminated drug-polymer coating 240 to the surrounding area in a body. The amount of drug eluted is determined as the total amount of therapeutic agent excreted out of laminated drug-polymer coating 240, typically measured in units of weight such as micrograms, or in weight per peripheral area of the stent. In another embodiment, barrier layers 244 and 248 include a second therapeutic agent such as camptothecin. In another embodiment, the concentration of the therapeutic agents in either drug-polymer layers 242 and 246 or barrier layers 244 and 248 are modulated to provide a predetermined drug-release profile. The concentration of the second therapeutic agent in barrier layers 244 and 248 may be between, for example, 0.1 percent and 50 percent by weight.

In another example of a multi-layer coated stent, drug-polymer layers 242 and 246 comprise a first polymer including a rigid thermoplastic polyurethane and an anti-proliferative therapeutic agent such as 5-fluorouracil, and barrier layers 244 and 248 include an ester-extended polyurethane. An example of a rigid thermoplastic polyurethane is TECOPLAST®, a hydrophobic polymer available from Thermedics Polymer Products in Wilmington, Mass. An example of an ester-extended polyurethane is TECOPHILIC®, a hydrophilic polymer also available from Thermedics Polymer Products in Wilmington, Mass. Barrier layers 244 and 248 may optionally include a therapeutic agent such as rapamycin, a rapamycin derivative, or a rapamycin analog. Alternatively, barrier layers 244 and 248 may include an anti-inflammatant such as dexamethasone.

In another example, drug-polymer layers 242 and 246 comprise a first polymer including a copolymer of methacrylamide, methacrylate, and vinyl alcohol with an anti-proliferative therapeutic agent such as 5-fluorouracil. Barrier layers 244 and 248 include a second polymer such as rigid thermoplastic polyurethane and may include an anti-inflammatant such as dexamethasone.

In another example, drug-polymer layers 242 and 246 comprise a first polymer including a copolymer of methacrylamide, methacrylate, and vinyl acetate with an anti-inflammatant such as dexamethasone. Barrier layers 244 and 248 include a second polymer such as poly(butyl methacrylate) (PBMA), and may include a second therapeutic agent such as 5-fluorouracil.

Figure 3:
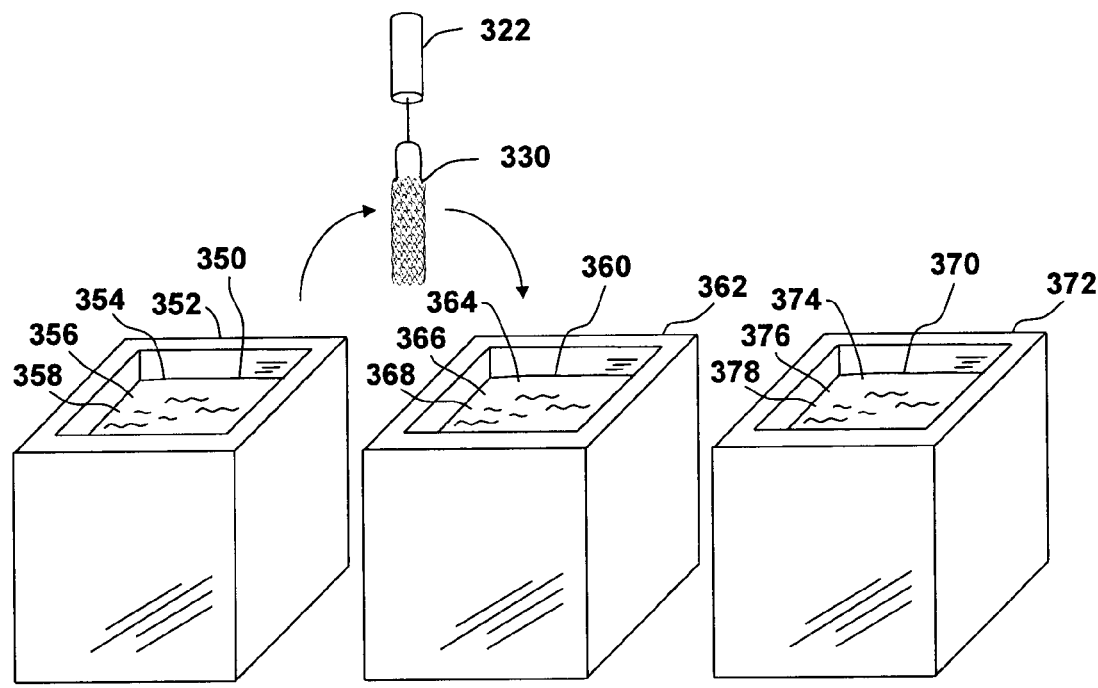
FIG. 3 is an illustration of a system for applying a drug-polymer coating on a stent, in accordance with one embodiment of the current invention.

FIG. 3 shows an illustration of a system for applying a drug-polymer coating on a stent, in accordance with one embodiment of the current invention at 300. Drug-polymer coating system 300 includes a first polymeric solution 350 in a first tank 352, a second polymeric solution 360 in a second tank 362, and a mechanism 322 such as a mandrel, a clamp, or a tether for holding and transporting stents in and out of a tank either manually or automatically. Multiple stent frameworks 330 are readily accommodated for dipping and drying in a batch or continuous batch process.

First polymeric solution 350 includes a first polymer 354, a first therapeutic agent 356, and a first solvent 358. Stent framework 330 can be dipped into first polymeric solution 350 and dried, for example, by positioning dipped stent framework 330 in air or in an oven and evaporating first solvent 358 to form a thin drug-polymer layer. Minimizing the solids content of first polymeric solution 350 can lower the viscosity, so that uniform coating and minimal or no bridging occurs across the apertures of stent framework 330.

Second polymeric solution 360 includes a second polymer 364 and a second solvent 368. Stent framework 330 with the first laminated drug-polymer layer can be dipped into second polymeric solution 360 and dried, for example, by positioning dipped stent framework 330 in an oven or in air for high throughput and evaporating second solvent 368 to form a thin barrier layer. Second polymeric solution 360 may include a second therapeutic agent 366 dissolved into second solvent 368. Low viscosity for minimizing bridging and webbing across the apertures of stent framework 330 can be obtained by minimizing the solids content of second polymeric solution 360.

A third polymeric solution 370 in a third tank 372 with a third polymer 374 and a third solvent 378 may be included with drug-polymer coating system 300. Third polymeric solution 370 may include a third therapeutic agent 376 dissolved in third solvent 378. In one example, third polymer 374 is the same as first polymer 354, third solvent 378 is the same as first solvent 358, and third therapeutic agent 376 is the same as first therapeutic agent 356, though at a higher or a lower concentration than first therapeutic agent 356 in first polymeric solution 350. In this case, the concentration of third therapeutic agent 376 disposed on stent framework 330 can be higher or lower than previously dipped and dried drug-polymer layers. The concentration of first therapeutic agent 356 in the drug-polymer layers can be modulated to provide a predetermined drug-release profile.

In another example, third polymer 374 is the same as second polymer 364, third solvent 378 the same as second solvent 368, and third therapeutic agent 376 is the same as second therapeutic agent 366 though at a higher or a lower concentration than second therapeutic agent 366 in second polymeric solution 360. The concentration of third therapeutic agent 376 disposed on stent framework 330 can be higher or lower than previously dipped and dried barrier layers, so that the concentration of second therapeutic agent 366 in the barrier layers can be modulated to provide a predetermined drug-release profile for second therapeutic agent 366 from a coated stent when deployed in a body.

In other examples, the concentrations of third polymer 374 in third polymeric solution 370 can be varied to adjust the viscosity, solids content, and subsequent thickness of drug-polymer layers or barrier layers within a drug-polymer coated stent, so that a predetermined drug-release profile of one or more therapeutic agents in the drug-polymer layers or the barrier layers can be provided.

Figure 4:
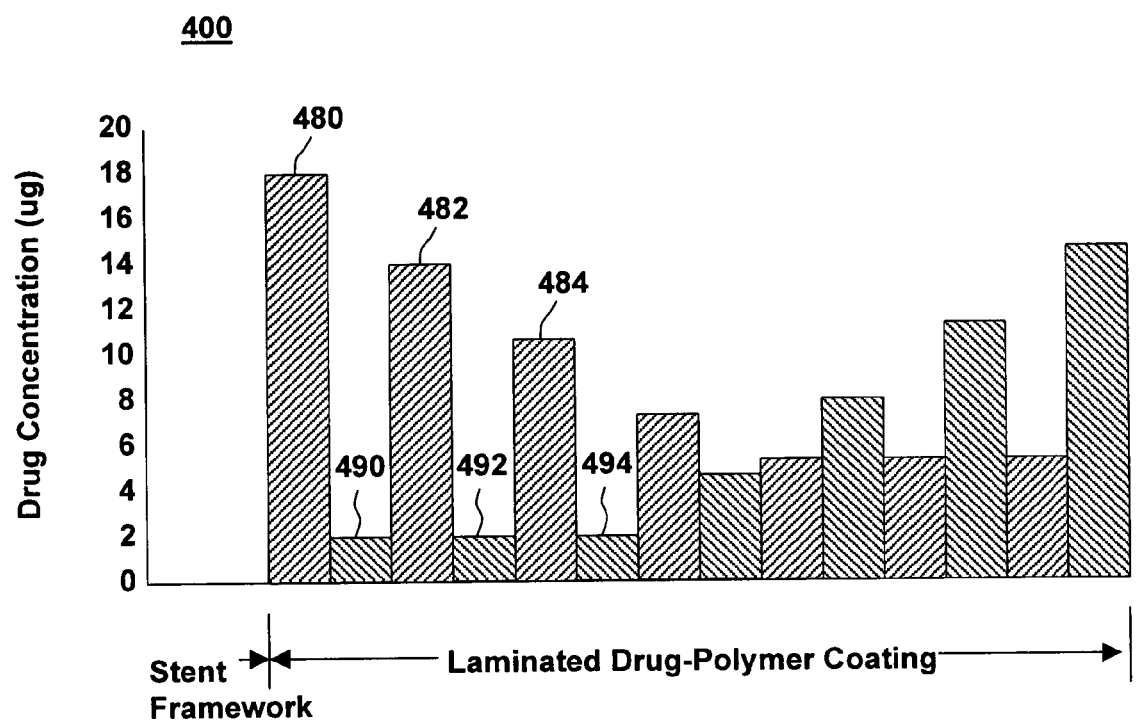
FIG. 4 is a graph of drug concentration in a laminated drug-polymer coated stent, in accordance with one embodiment of the current invention.

FIG. 4 shows a graph of drug concentration in a laminated drug-polymer coated stent, in accordance with one embodiment of the present invention at 400. An exemplary coated stent has a laminated drug-polymer coating with a plurality of thin drug-polymer layers positioned between thin barrier layers. The drug-polymer layers include a therapeutic agent and a first polymer, and the barrier layers include a second polymer. The barrier layers may include a second therapeutic agent.

The laminated drug-polymer coatings on the coated stent elute at least one therapeutic agent. Alternatively, the laminated drug-polymer coating may include and elute multiple therapeutic agents. The thickness of the individual layers, the types of polymers selected, and the concentration of the therapeutic agents, among other factors, can be tailored to control the elution of one or more therapeutic agents from the coated stent. Elution of therapeutic agents occurs primarily by diffusion processes. In some cases, a portion of the laminated drug-polymer coating is absorbed into the body to release the therapeutic agents. In other cases, a portion of polymeric coating erodes away to release the therapeutic agents.

In this exemplary embodiment, a plurality of drug-polymer layers 480, 482 and 484 include a first therapeutic agent with a modulated concentration to provide a predetermined drug-release profile, and a plurality of thin barrier layers 490, 492 and 494 include a second therapeutic agent with a modulated concentration. Drug-polymer layers close to the stent framework, in this example, have a higher concentration of the first therapeutic agent than drug-polymer layers near the outside of the laminated drug-polymer coating. Barrier layers close to the stent framework have a lower concentration of the second therapeutic agent than barrier layers near the outside of the laminated drug-polymer coating. In another embodiment, the barrier layers contain no therapeutic agents. In other embodiments, the concentrations of the first therapeutic agents and the second therapeutics along with the thickness of the drug-polymer layers and the barrier layers are varied to achieve a predetermined drug-release profile for each of the therapeutic agents.

Figure 5:
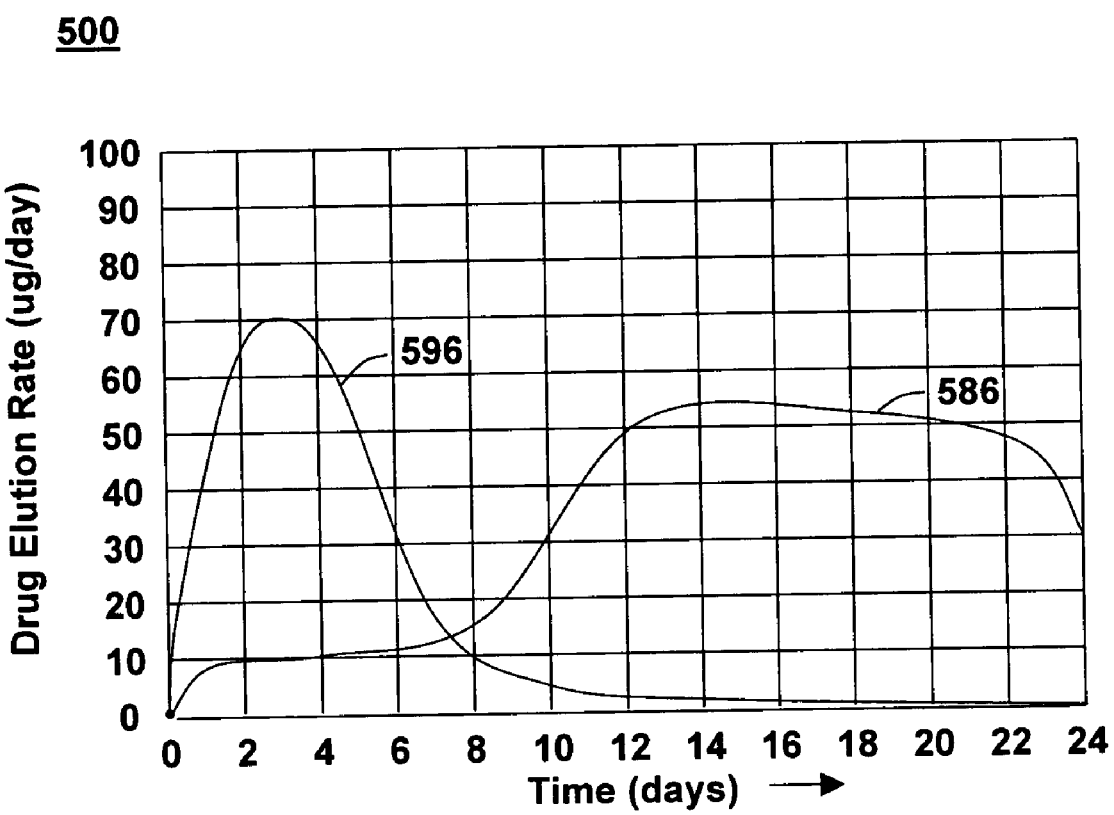
FIG. 5 is a graph of drug elution rate from a drug-polymer coated stent, in accordance with one embodiment of the current invention.

FIG. 5 shows a graph of drug elution rate from a drug-polymer coated stent, in accordance with one embodiment of the present invention at 500. Drug elution rate graph 500 shows a characteristic curve 586 representing the elution of a first therapeutic agent into the body after the coated stent is deployed. After deployment into the body, the first therapeutic agent is eluted from the laminated drug-polymer coating in a predetermined profile, with a small amount of the first therapeutic agent released within the first several days, and increasing to a higher delivery rate in a following period of weeks or months until the therapeutic agent is completely eluted. The elution rate may be determined from a graph that represents the total drug eluted by taking the derivative with respect to time, or by dividing the amount of drug eluted over a specified time interval by the elapsed time.

Drug elution rate graph 500 also shows a characteristic curve 596 representing the elution of a second therapeutic agent into the body. After deployment into the body, the second therapeutic agent is eluted from the laminated drug-polymer coating in a predetermined profile, with a large amount of the second therapeutic agent released within the first few hours and days, and then the rate of release rapidly falling off after that.

An elution rate for each therapeutic agent can be predetermined by a careful selection of the concentration of each therapeutic agent in the thin drug-polymer layers and the thin barrier layers; the thickness of the individual drug-polymer layers and the barrier layers; the polymers and polymeric blend in the drug-polymer layers and the barrier layers; and the total number of layers.

Figure 6:
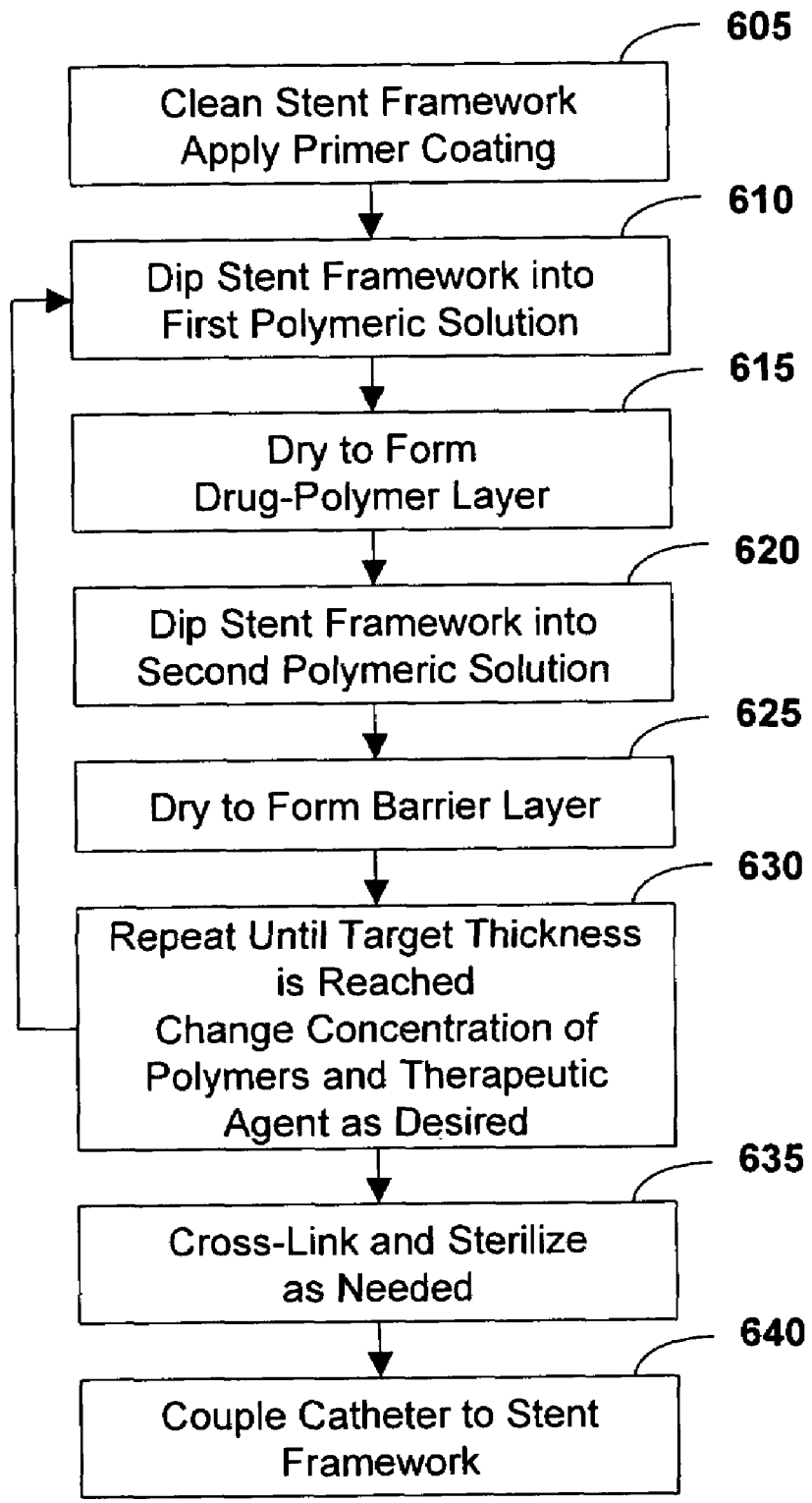
FIG. 6 is a flow diagram of a method of applying a drug-polymer coating on a stent, in accordance with one embodiment of the current invention.

FIG. 6 shows a flow diagram of a method of applying a drug-polymer coating on a stent, in accordance with one embodiment of the present invention at 600. Drug-polymer application method 600 includes various steps to form a laminated drug-polymer coating on a stent framework, and to provide a predetermined drug-release profile when the coated stent is deployed in the body.

A stent framework is cleaned, as seen at block 605. The stent framework may be cleaned, for example, by inserting the stent framework into various solvents, degreasers and cleansers to remove any debris, residues, or unwanted materials from the surface of the stent framework. The stent framework is dried, and generally inspected at this point in the process.

After cleaning, a primer coating may be disposed on the stent framework, particularly to metallic stent frameworks such as stainless steel, assisting in the adhesion of the laminated drug-polymer coating to the stent framework. The primer coating may include, for example, the application of a suitable primer layer such as parylene, polyurethane, phenoxy, epoxy, polyimide, polysulfone, or pellathane. The primer coating may be applied to the stent framework by dipping, spraying, painting, brushing, or other suitable methods. The primer coating is dried and cured or cross-linked as needed for eliminating or removing any volatile components. Excess liquid may be blown off prior to drying the primer coating, which may be done at room temperature or elevated temperatures under a dry nitrogen or other suitable environment including a vacuum environment.

The stent framework is dipped into a first polymeric solution, as seen at block 610. The first polymeric solution comprises a first polymer, a first therapeutic agent, and a first solvent. One or more therapeutic agents may be mixed with the first polymeric solution prior to its application onto the stent framework. The mixture can be created by adding the therapeutic agents directly into the first polymeric solution. Alternatively, the mixtures can be created by dissolving the therapeutic agents in a therapeutic agent solution comprising a suitable solvent, and then adding and mixing them with the polymeric solution.

In one example, the first polymer of poly(ethylene-vinyl acetate) (PEVA), and the first therapeutic agent of camptothecin are dissolved in a first solvent that includes a mixture of chloroform and methanol. The camptothecin is dissolvable in other solvents such as a mixture of ethanol, chloroform and methanol. The first polymeric solution may comprise, for example, between 0.05 percent and 3.0 percent and up to 10 percent or more total solids by weight of the first polymer, selected to provide a low-viscosity solution so that very thin layers of the polymer and therapeutic agent may be disposed on the stent framework that can avoid webbing and bridging between the openings in the stent framework. In another example, the first therapeutic agent comprises rapamycin, a rapamycin derivative, or a rapamycin analog. In a currently preferred embodiment, the solvent has a chloroform concentration between 80 percent and 90 percent, with methanol comprising the balance. The rapamycin and associated compounds are soluble in other solvents, such as acetones, heptanes, methyl tertiary-butyl ether (MTBE), methylene chloride (MEC), tetrahydrofuran (THF), and isopropyl alcohol.

In another example, the first polymeric solution includes a rigid thermoplastic polyurethane and a therapeutic agent such as 5-fluorouracil in a blend of tetrafuran and methanol. The concentration of total solids by weight of the first polymer in the solvent ranges between 0.05 percent and 10.0 percent, with a presently preferred range between 0.1 percent and 3.0 percent. The concentration of the therapeutic agent in the dried layer may range between 0.1 percent and 50 percent or greater. The concentration of tetrahydrofuran in the solvent may range between 10 percent and 90 percent or greater, with a presently preferred concentration of 80 percent tetrahydrofuran and methanol comprising the balance.

In another example, a copolymer of methacrylamide, methacrylate and vinyl alcohol are mixed with 5-fluorouracil in chloroform and water. In another example, a copolymer of methacrylamide, methacrylate and vinyl acetate are mixed with dexamethasone in ethanol.

The first polymeric solution is dried to form a thin drug-polymer layer on the stent framework, as seen at block 615. The dipped stent framework may be dried, for example, by positioning the dipped stent framework in air after dipping the stent framework into the first polymeric solution, and evaporating the first solvent prior to dipping the stent framework in the next polymeric solution. The first polymeric solution is generally dried after application by evaporating off the solvent at room temperature and under ambient conditions. A nitrogen environment or other controlled environment may also be used for drying. Alternatively, the first polymeric solution can be dried by evaporating the majority of the solvent at room temperature, and then further dried in a vacuum environment between, for example, a room temperature of about 25 degrees centigrade and 45 degrees centigrade or higher to extract any pockets of solvent buried within the drug-polymer layer. Vacuum drying, heated convective air, forced air or hot air, heated convective nitrogen, forced nitrogen or forced heated nitrogen or other suitable drying methods and combinations thereof for full or partial drying may be used.

The stent framework including the drug-polymer layer is dipped into a second polymeric solution, as seen at block 620. The second polymeric solution includes a second polymer and a second solvent, the second solvent selected so that the drug-polymer layer dried on the stent framework is insoluble in the second polymeric solution. The polymers and therapeutic agents in the drug-polymer layers and the thin barrier layers may be selected to be marginally soluble or insoluble in the respective solvents that are used.

The second polymer may be selected, for example, with a low glass temperature and a low affinity for the drugs or therapeutic agents in the drug-polymer layer. The second polymeric solution may comprise, for example, between 0.05 percent and 3.0 percent and up to 10.0 percent or more total solids by weight of the second polymer, selected to provide a low-viscosity solution so that thin barrier layers of the second polymer may be disposed on the stent framework. The stent framework with the first drug-polymer layer can be dipped into the second polymer solution without impacting the content of the initial layer. In one example, the second polymer comprises polyurethane. In another example, the second polymer comprises polycaprolactone. In another example, the second polymer comprises a blended polymer of polyurethane and polycaprolactone. The second solvent comprises, for example, tetrahydrofuran. The second polymeric solution may comprise a second therapeutic agent such as camptothecin mixed into or added to the second polymeric solution.

In another example, the second polymeric solution includes an ester-extended polyurethane mixed in chloroform. Optionally, an anti-proliferative compound such as rapamycin, a rapamycin derivative, or a rapamycin analog may be mixed into the second polymeric solution. Alternatively, dexamethasone or other anti-inflammatant may be mixed into the second polymeric solution. The concentration of the polymers in the solvent may range, for example, between 0.05 percent and 3.0 percent and up to 10.0 percent or more. The concentration of the rapamycin, rapamycin derivative or rapamycin analog ranges, for example, between 0.1 percent and 50 percent by weight in the dried layer.

In another example, the second polymeric solution includes a rigid thermoplastic polyurethane dissolved in tetrahydrofuran. An anti-inflammatant such as dexamethasone may optionally be mixed into the solution.

In another example, the second polymeric solution includes poly(butyl methacrylate) dissolved in a blend of tetrahydrofuran and methanol. An anti-proliferative compound such as 5-fluorouracil may optionally be mixed into the solution.

The second polymeric solution is dried to form a thin barrier layer on the stent framework, as seen at block 625. The barrier layer is substantially insoluble in the first polymeric solution, so that when subsequent layers of drug-polymer layers are formed on the stent framework, underlying barrier layers are neither dissolved nor eroded away. The barrier layer may be selected to provide a diffusion barrier to the drug in the drug-polymer layer and slow down drug elution.

After the stent framework has been dipped into the second polymeric solution, the second polymeric solution may be dried, for example, in an oven at an elevated temperature, or by positioning the dipped stent framework in air at room temperature, and evaporating the second solvent prior to dipping the framework into the next polymeric solution. Vacuum drying, heated convective air, forced air or hot air, heated convective nitrogen, forced nitrogen or forced heated nitrogen or other suitable drying methods and combinations thereof for full or partial drying may be used.

The steps of dipping the stent framework into the first polymeric solution, drying the first polymeric solution, dipping the stent framework into the second polymeric solution, and drying the second polymeric solution are repeated until a target drug-polymer coating thickness is disposed on the stent framework, as seen at block 630. Multiple dipping and drying steps are used to provide an appropriate coating weight and avoid webbing or bridging of the apertures between the struts in the stent framework. Repeatedly applying thin drug-barrier layers and thin barrier layers allows for uniform, defect-free dip-coated items. The concentration of the first therapeutic agent in the first polymeric solution may be changed between the dipping and drying steps to modulate the concentration of the first therapeutic agent in the drug-polymer layers and provide a predetermined drug-release profile. The concentration of the second therapeutic agent in the second polymeric solution, when used, may also be changed between dipping and drying steps, providing a different concentration of the second therapeutic agent in the barrier layers and providing a predetermined drug-release profile. Different drug concentrations in the drug-polymer layers can be selected to provide a tailored elution curve, and the barrier layers may help to preserve and prolong the elution of the drugs. The chosen composition of the thin barrier layers can be highly permeable to one or more of the therapeutic agents. For example, a second polymer with a lower or higher glass transition temperature than the first polymer may be selected to control the elution rate.

The coated stent with the laminated drug-polymer coating may be cross-linked and sterilized as needed, as seen at block 635. Cross-linking may be done by providing additional drying cycles in air, or by heating the coated stent above a curing temperature in an oven with a controlled ambient such as vacuum, nitrogen, or air. Sterilization may employ, for example, gamma-ray irradiation, e-beam radiation, ethylene oxide gas, or hydrogen peroxide gas plasma sterilization techniques. With appropriate selection of the barrier layer polymer, for example, selective cross-linking of the barrier layer polymer may occur during sterilization while the drug-polymer layer remains unaffected. The coated stent may be packaged, shipped, and stored in a suitable package until it is used.

A delivery catheter may be coupled to the coated stent, as seen at block 640. The delivery catheter may include an inflatable balloon that is positioned between the coated stent and the catheter and used for deploying the coated stent in the body. Alternatively, the delivery catheter may include a sheath that retracts to deploy a self-expanding version of the coated stent.

In one exemplary method, fully processed coated stents are reduced in diameter and placed into the distal end of the catheter to form an interference fit, which secures the stent onto the catheter. The catheter with the stent may be placed in a catheter package and sterilized prior to shipping and storing. Before clinical use, the stent is sterilized by any appropriate or medically conventional means.

Alternative ordering of process steps or variants of the method for applying a drug-polymer coating on a stent can be employed. For example, a barrier layer can be applied to the stent framework before a drug-polymer layer by dipping the framework into the second polymeric solution before dipping it into the first polymeric solution, which contains one of more of the therapeutic agents. Other embodiments of the present invention include switching the order of the drug-polymer layers and the barrier layers, dipping multiple times into the same bath to thicken a layer, dipping the coated stent into additional baths with adjusted concentrations of therapeutic agents to achieve a desired elution profile, and adjusting the temperature of each bath.

FIG. 7 shows a flow diagram of a method for treating a vascular condition, in accordance with one embodiment of the present invention at 700. Vascular condition treatment method 700 includes steps to insert a drug-polymer coated stent within a vessel of a body and to elute at least one therapeutic agent from the drug-polymer coated stent into the body. One or more therapeutic agents are included or interdispersed within thin drug-polymer layers and thin barrier layers of the laminated drug-polymer stent coating.

The first and second polymers and their respective concentrations are selected based on a predetermined elution rate of each therapeutic agent, as seen at block 710. The solvents and concentrations of polymers and therapeutic agents are also selected to prevent dissolution of dried polymers and drugs of previously applied layers with subsequent dipping and drying of additional drug-polymer layers and barrier layers. The fractional constituencies of the polymers and therapeutic agents are selected to achieve an intended pharmaceutical intent, such as a predetermined elution rate for one or more therapeutic agents within the laminated drug-polymer coating. One or more therapeutic agents are included in the drug-polymer layers, and one or more therapeutic agents may be included in the barrier layers. The laminated drug-polymer layers and barrier layers are selected to control the elution rate of each therapeutic agent and the total quantity of each drug delivered.

A coated stent with a laminated drug-polymer coating is fabricated by using selected polymers, therapeutic agents, solvents and concentrations thereof, as seen at block 720. The laminated drug-polymer coating has a plurality of thin drug-polymer layers positioned between thin barrier layers. The drug-polymer layers include a therapeutic agent and a first polymer, and the thin barrier layers include a second polymer. A primer coating may be included to improve the adhesion between the stent framework and the coating layers.

When ready for deployment, the drug-polymer coated stent with the selected polymers, therapeutic agents, solvents and concentrations is inserted into a vessel of the body, as seen at block 730. The drug-polymer coated stent is inserted typically in a controlled environment such as a catheter lab or hospital. A delivery catheter, which helps position the drug-polymer coated stent in a vessel of the body, is typically inserted through a small incision of the leg and into the femoral artery, and directed through the vascular system to a desired place in the vessel. Guide wires threaded through an inner lumen of the delivery catheter assist in positioning and orienting the drug-polymer coated stent. The position of the drug-polymer coated stent may be monitored, for example, with a fluoroscopic imaging system or an x-ray viewing system in conjunction with radiopaque markers on the coated stent, radiopaque markers on the delivery catheter, or contrast fluid injected into an inner lumen of the delivery catheter and into an inflatable catheter balloon that is coupled to the drug-polymer coated stent. The stent is deployed, for example, by expanding the stent with a balloon or by extracting a sheath that allows a self-expandable stent to enlarge after positioning the stent at a desired location within the body. Before clinical use, the stent is sterilized by using conventional medical means.

Once deployed, the therapeutic agents in the laminated drug-polymer coating are eluted, as seen at block 740. The elution rates of the selected therapeutic agents into the body and the tissue bed surrounding the stent framework are based on the polymers, thickness of the drug-polymer layers and barrier layers, and the concentration of the therapeutic agents contained therein, among other factors.

Although the present invention applies to cardiovascular and endovascular stents with timed-release therapeutic agents, the use of laminated drug-polymer coatings may be applied to other implantable and blood-contacting biomedical devices such as coated pacemaker leads, microdelivery pumps, feeding and delivery catheters, heart valves, artificial livers and other artificial organs.

While the embodiments of the invention disclosed herein are presently considered to be preferred, various changes and modifications can be made without departing from the spirit and scope of the invention. The scope of the invention is indicated in the appended claims, and all changes that come within the meaning and range of equivalents are intended to be embraced therein.

What is claimed is:

1. A method of applying a drug-polymer coating on a stent, comprising:
    dipping a stent framework into a first polymeric solution, wherein the first polymeric solution comprises a first polymer, a first therapeutic agent, and a first solvent, wherein the first polymer comprises a copolymer of methacrylamide, methacrylate and vinyl alcohol, the first therapeutic agent comprises 5-fluorouracil, and the first solvent comprises a mixture of chloroform and water;
    drying the first polymeric solution to form a thin drug-polymer layer on the stent framework;
    dipping the stent framework including the thin drug-polymer layer into a second polymeric solution, wherein the second polymeric solution comprises a second polymer and a second solvent, wherein the thin drug-polymer layer is insoluble in the second polymeric solution, and wherein the second polymer comprises a rigid thermoplastic polyurethane and the second solvent comprises tetrahydrofuran;
    drying the second polymeric solution to form a thin barrier layer on the first thin drug-polymer layer; and
    repeating the steps of dipping the stent framework into the first polymeric solution, drying the first polymeric solution, dipping the stent framework into the second polymeric solution, and drying the second polymeric solution until a target drug-polymer coating thickness is disposed on the stent framework.

2. The method of claim 1 wherein the first polymeric solution comprises between 0.05 percent and 10.0 percent total solids by weight of the first polymer.

3. The method of claim 1 wherein the second polymeric solution comprises an anti-inflammatant.

4. The method of claim 1 wherein the second polymeric solution comprises dexamethasone.

5. The method of claim 1 wherein the thin barrier layer is insoluble in the first polymeric solution.

6. The method of claim 1 wherein drying the first polymeric solution comprises positioning the dipped stent framework in air after dipping the stent framework into the first polymeric solution, and evaporating the first solvent.

7. The method of claim 1 wherein drying the second polymeric solution comprises positioning the dipped stent framework in air after dipping the stent framework into the second polymeric solution, and evaporating the second solvent.

8. The method of claim 1 further comprising:
    modulating a concentration of the first therapeutic agent in the thin drug-polymer layers to provide a predetermined drug-release profile.

9. A method of applying a drug-polymer coating on a stent, comprising:
    dipping a stent framework into a first polymeric solution, wherein the first polymeric solution comprises a first polymer, a first therapeutic agent, and a first solvent, wherein the first polymer comprises a copolymer of methacrylamide, methacrylate and vinyl acetate; the first therapeutic agent comprises dexamethasone; and the first solvent comprises ethanol;
    drying the first polymeric solution to form a thin drug-polymer layer on the stent framework;
    dipping the stent framework including the thin drug-polymer layer into a second polymeric solution, wherein the second polymeric solution comprises a second polymer and a second solvent, wherein the second polymer comprises poly(butyl methacrylate); and the second solvent comprises a blend of tetrahydrofuran and methanol, and wherein the thin drug-polymer layer is insoluble in the second polymeric solution;
    drying the second polymeric solution to form a thin barrier layer on the first thin drug-polymer layer; and
    repeating the steps of dipping the stent framework into the first polymeric solution, drying the first polymeric solution, dipping the stent framework into the second polymeric solution, and drying the second polymeric solution until a target drug-polymer coating thickness is disposed on the stent framework.

10. The method of claim 9 wherein the second polymeric solution comprises an anti-proliferative compound.

11. The method of claim 9 wherein the second polymeric solution comprises 5-fluorouracil.

* * * * *